United States Patent [19]

Csuták et al.

[11] Patent Number: 4,866,043
[45] Date of Patent: Sep. 12, 1989

[54] SEED DRESSING COMPOSITION BASED ON A PHOSPHONIC ACID MONOESTER SALT

[75] Inventors: Janos Csuták; András S. Kiss; Kálmán Marossy; Vilma Széchy, all of Kazincbarcika; Maria Kocsis née Bágyi; Katalin Görög née Privitzer, both of Budapest; László Bodnár, Budaörs; György Kiss, Budapest; Mária Lipták, Halásztelek; Cserháti née Botka, Balassagyarmat; János Wábel; Tibor Halmágyi, both of Békéscsaba; Lajos Kadenczky; Zoltan Árpád, both of Miskolc; Katalin Mármarosi née Kellner, Biatorbágy; Katalin Kecskés née Iván, Kazincbarcika, all of Hungary

[73] Assignee: Borsodi Vegyi Kombinát, Kazincbarcika, Hungary

[21] Appl. No.: 72,804

[22] Filed: Jul. 14, 1987

Related U.S. Application Data

[63] Continuation-in-part of Ser. No. 778,570, Sep. 20, 1985, abandoned.

[30] Foreign Application Priority Data

Sep. 21, 1984 [HU] Hungary .................. 3548/84

[51] Int. Cl.[4] .................................................. A01C 1/06
[52] U.S. Cl. .................................. 514/75; 47/57.6; 47/DIG. 9; 71/77
[58] Field of Search ............ 514/75; 47/57.6, DIG. 9; 71/3, 77

[56] References Cited

U.S. PATENT DOCUMENTS 4,193,993 3/1980 Hilditch .................. 424/145
4,366,150 12/1982 Yamada .................. 514/75

FOREIGN PATENT DOCUMENTS 56-71001 6/1981 Japan .................. 514/75

Primary Examiner—Mark L. Bell
Attorney, Agent, or Firm—Schweitzer & Cornman

[57] ABSTRACT

The invention relates to a seed dressing composition containing 20 to 90% of 3-isononyloxypropyl-ammonium methyl phosphonate as active ingredient, optionally 2 to 10% by weight of a metal ion, preferably magnesium or zinc ion as well as a solid carrier and optionally other additives, preferably a surface active agent and/or adhesion promoting agent, in amounts adding up to 100% by weight, and to a method of protecting seeds against fungus attack by the application thereto of said composition.

12 Claims, 3 Drawing Sheets

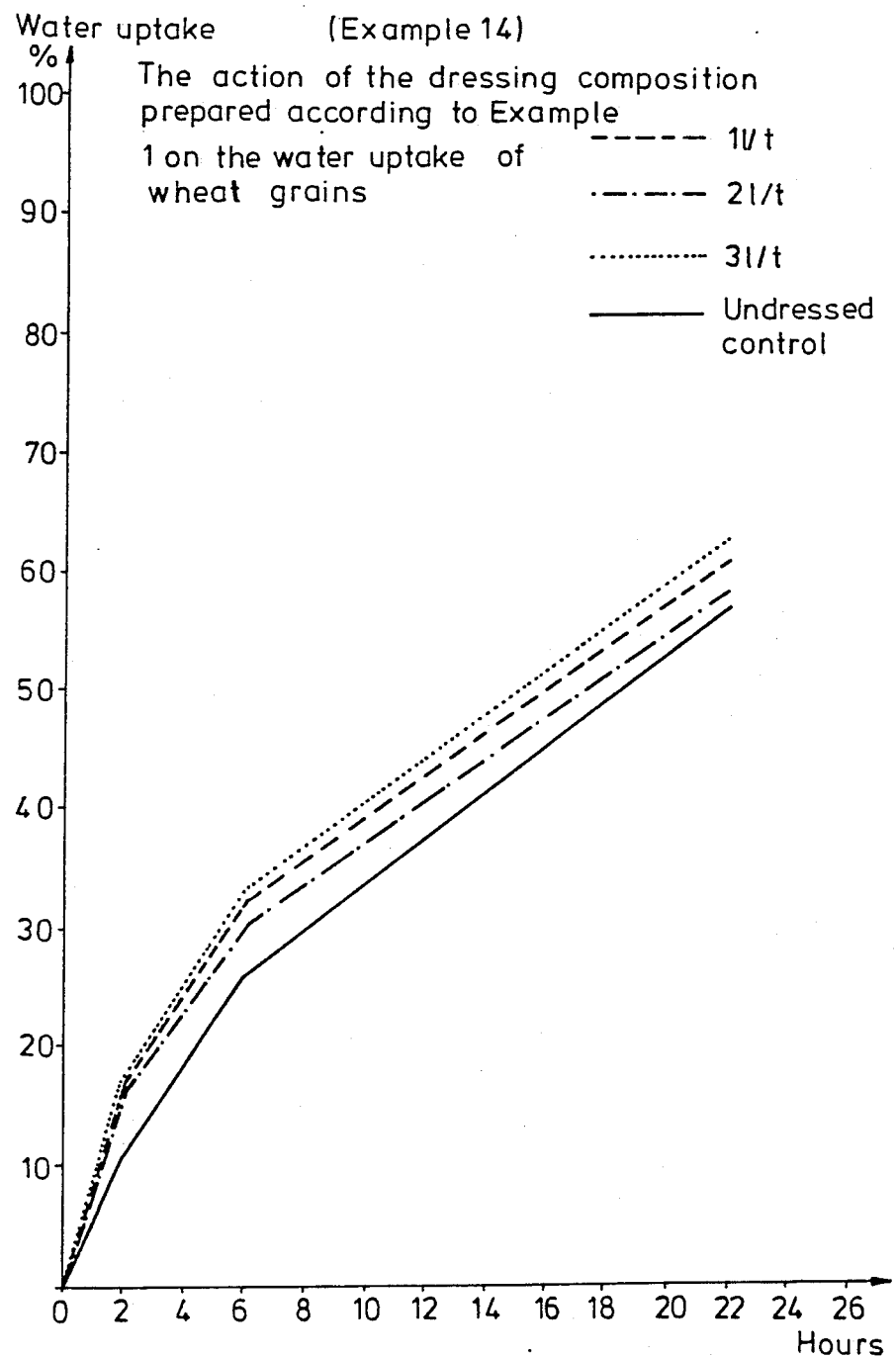
Fig. 1/a

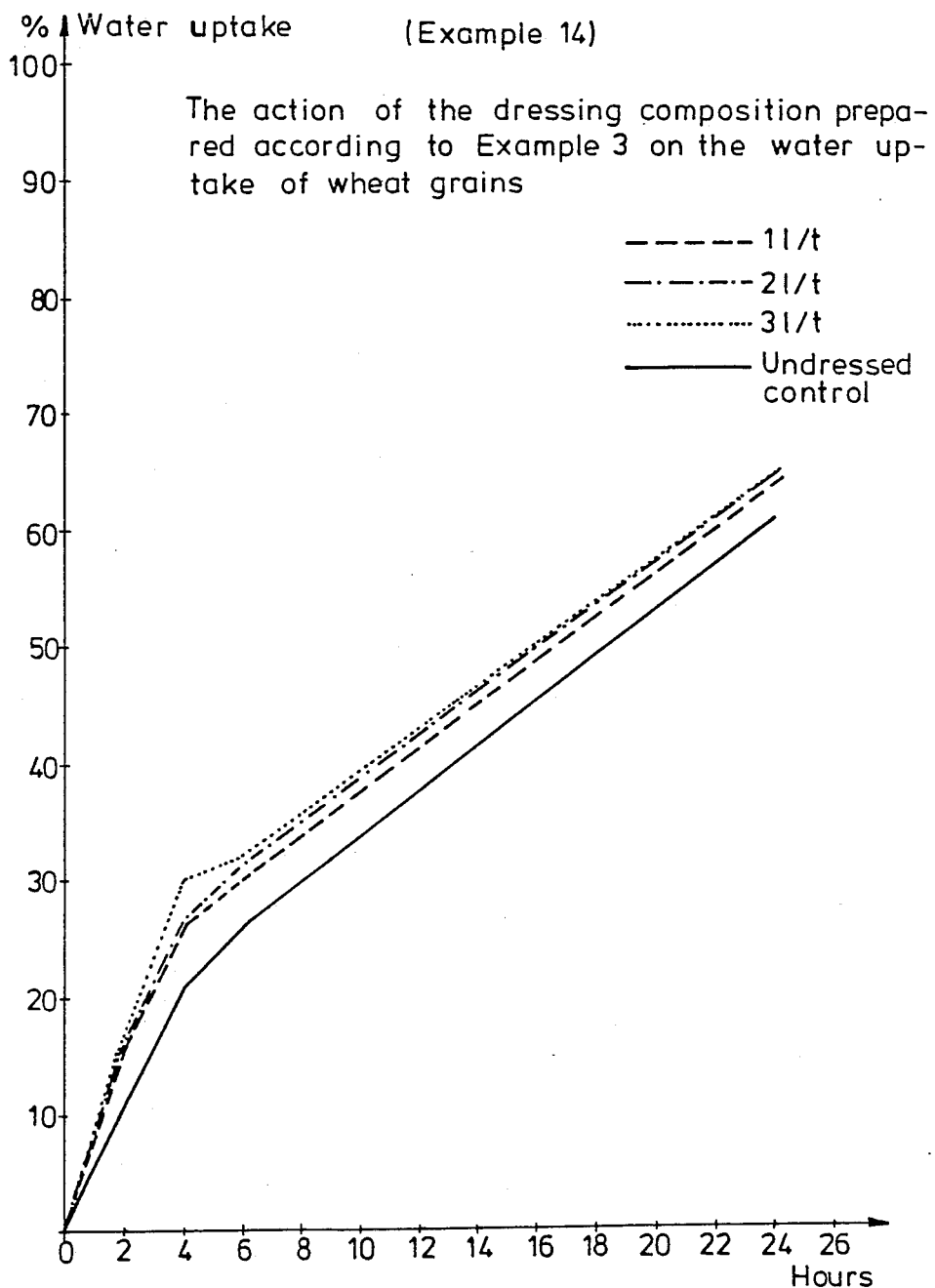
Fig. 1/b

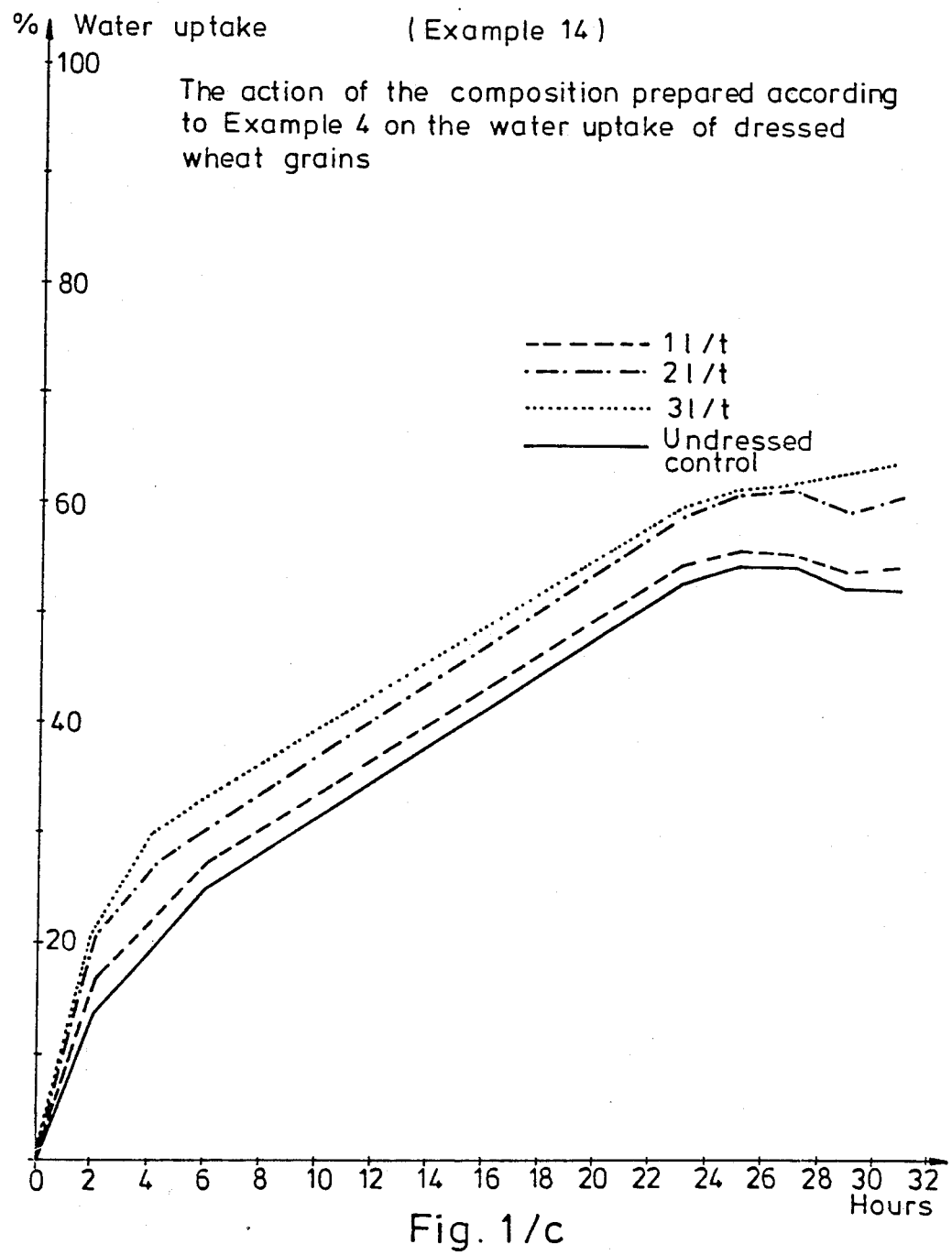
Fig. 1/c

SEED DRESSING COMPOSITION BASED ON A PHOSPHONIC ACID MONOESTER SALT

RELATED APPLICATION

This application is a continuation-in-part of application Ser. No. 778,570, filed Sept. 20, 1985, now abandoned.

The invention relates to seed dressing compositions containing 20 to 90% by weight of 3-isononyloxypropyl-ammonium methyl phosphonate as the active ingredient, 2 to 10% by weight of a metal iron, preferably magnesium or zinc ion, a solid or liquid carrier and optionally other additives, preferably a surface active agent and/or an adhesion promoting agent.

The preparation of 3-isononyloxypropyl-ammonium methyl phosphonate as well as its use as the active ingredient in fungicidal compositions is reported in the Hungarian patent specification No. 184,319. However, the use of this active agent as the active ingredient of a seed dressing composition is not mentioned.

It is also disclosed in DE-OS No. 2,456,627 that aluminium ethyl phosphonate has an excellent fungicidal activity. Once again, however, it is not utilized as an active ingredient in seed dressing compositions.

Surprisingly, it has been found that, in contrast to aluminium ethyl phosphonate, 3-isononyloxypropyl-ammonium methyl phosphonate, when present in an appropriate concentration, is very useful for protecting cereals, e.g., corn, maize, and barley, other field-cultivated plants, e.g., sugar beet, sunflower, and soy, and horticultural plants, e.g., paprika, against diseases of the germinative period, e.g. Fusariosis, Rhyzoctonia diseases, etc. The compound also provides protection against pathogens, e.g., mildew and black-rust which are spread with the sowing-seed but appear in the crop-ripening period. In contrast, 3-isononyloxypropyl-ammonium ethyl phosphonate reported in the Hungarian patent specification No. 184,319 is noted to inhibit germination so as to be unavailable for use in seed dressings.

The protecting action of the active agent of the invention is exerted by a double effect:

On the one hand, it has a direct fungicidal effect on the pathogens whereby those living in the soil or on the surface of the seeds are destroyed;

On the other hand, it is absorbed into the seed whereby the endoparasites are also killed.

The advantageous dressing action can also be explained by the fact the water balance of seeds dressed with the composition of the invention shows a better development as compared to untreated seed. The importance of the increase in water absorption is reflected in that the germination is accelerated such that the seedling phase, which is sensitive to pathogens, becomes shorter.

As mentioned above, the advantageous effects which can be achieved by using the composition containing 3-isononyloxypropyl-ammonium methyl phosphonate as active ingredient are noted when using appropriate concentrations. Although higher concentrations may cause seedling-damaging effects, it has been observed that such seedling-damaging effects can be prevented by using a metal ion in combination with the active ingredient. Germination-inhibiting effects of 3-isononyloxypropyl-ammonium ethyl phosphonate are, however, experienced when the concentration is so high that it cannot be prevented even by using a metal ion.

Accordingly, it has been found that an advantageous seed dressing action is also provided by using a higher active ingredient concentration in the composition of the invention when, in addition to the active ingredient, metal ions, preferably magnesium or zinc ions, are also employed. The compositions of the invention may thus contain 2 to 10%, by weight, preferably 2 to 5% by weight of a metal ion, preferably magnesium or zinc ion.

The invention also relates to a treating process for dressing seeds, which comprises treating the seeds with a composition containing 3-isononyloxypropyl-ammonium methyl phosphonate as active ingredient in an amount of 0.5 to 3 liters of active ingredient/ton or 0.5 to 3 kg of active ingredient/ton, optionally 2 to 10% by weight of a metal ion as well as a solid or liquid carrier and optionally other additives in an amount adding up to 100% by weight.

According to another embodiment of the invention, the seeds may be separately contacted with the composition containing 3-isononyloxypropyl-ammonium methyl phosphonate and with the composition containing the metal ion such that the composition containing 3-isononyloxypropyl-ammonium methyl phosphonate is used in an amount of 0.5 to 3 liters of active ingredient/ton or 0.5 to 3 kg of active ingredient/ton and the composition containing the metal ion is applied in an amount of 0.001 to 0.3 kg/ton.

Before application, the active ingredients of the invention are formulated into composition form by using solid or liquid carriers and optionally other additives, preferably surface active and adhesion promoting agents.

Suitable carriers include inert, agriculturally acceptable organic or mineral, natural or synthetic substances which promote the adsorption of the active ingredient onto the seed or the absorption of the active ingredient into the seed, e.g., water, alcohols such as methanol, glycerol, hydrocarbon solvents such as xylene, and the like, or mixture thereof. Such carriers will generally be present in concentrations ranging from 10 to 80%, by weight, and from 5–70%, by weight, when optional ingredients are present.

Suitable surface active agents include ionic or nonionic emusifying dispersing and wetting agents, preferably alkylaryl polyglycol ethers, fatty acid polyglycol esters, and ligninsulphonate salts. Suitable adhesion promoting agents are, e.g., partially hydrolyzed polyvinyl acetate, polyvinyl alcohol, carboxymethylcellulose and acacia gum. The suface active agents may be present in concentrations of from 0–5%, by weight, while the adhesion-promoting agents will be present in concentrations of from 0–16.5%, by weight.

The compositions of the invention can be formulated as water soluble concentrates (WSC), solutions, emulsifiable concentrates (EC) and wettable powders (WP).

Further details of the invention are illustrated by the following non-limiting examples. In these examples, BF-51 means 3-isononyloxypropyl-ammonium methyl phosphonate and BF-52 means 3-isononyloxypropyl-ammoniu ethyl phosphonate.

Aliette 70 WP, a fungidical composition containing aluminum ethyl phosphonate was used for comparison. The active ingredient of Quinolate-V-4-X is the copper complex of 8-hydroxyquinoline. Buvisild K is a composition described in the published Hungarian patent application No. BU-902.

EXAMPLE 1

175 g of polyvinyl alcohol (molecular weight 20000 to 30000) are dissolved in 825 ml of water at 35° to 40° C. After cooling, 50 ml of methanol and then 264 g of BF-51 are mixed in under continuous stirring. The thus obtained composition contains 20% by weight of active ingredient.

EXAMPLE 2

240 g of partially (up to about 70%) hydrolyzed polyvinyl acetate are dissolved in 950 ml of warm methanol, whereupon 264 g of BF-51 are mixed in. The thus obtained composition contains 20% by weight of active ingredient.

EXAMPLE 3

200 g of acacia gum are dissolved in 800 ml of hot water, 0.5 g of sodium benzoate is then added and the solution is filtered as hot. To the filtered and cooled solution, 50 ml of methanol and 264 g of BF-51 are added. The composition is prepared as described in Example 1. The thus obtained composition contains 20% by weight of active ingredient.

EXAMPLE 4

90% by weight of BF-51, 5% by weight of Emulsogen NO90 (alkylaryl polyglycol ether—a product of Hoechst AG) emulsifying agent and 5% by weight of methanol are thoroughly mixed to tive a 90 WSC formulation.

EXAMPLE 5

A wettable powder (WP) composition is prepared from the following components in a manner known in the art:

| | % by weight |
|---|---|
| BF-51 | 50 |
| Ultrasil VN 3, a silicate | 42.5 |
| Zinc acetate | 5 |
| Arkopal NO80 (nonylphenol polyglycol ether) | 2.5 |

EXAMPLE 6

A wettable powder (WP) composition is prepared from the following components:

| | % by weight |
|---|---|
| BF-51 | 50 |
| Ultrasil VN 3 | 37.5 |
| Magnesium sulphate | 5 |
| Carboxymethylcellulose | 5 |
| Arkopal N 110 (nonylphenol polyglycol ether) | 2.5 |

EXAMPLE 7

An emulsifiable concentrate (EC) composition is prepared from the following components:

| | % by weight |
|---|---|
| BF-51 | 60 |
| Atlox 4857 B (a mixture of ionic and nonionic tensides) | 3 |

-continued

| | % by weight |
|---|---|
| Xylene | 37 |

EXAMPLE 8

| | % by weight |
|---|---|
| BF-51 | 50 |
| Glycerol | 50 |

INVESTIGATIONS ON ACTIVITY METHODS (a) Before germinating in wet chambers, the seeds were dressed with the substances to be tested and the germination was carried out on a wet filter paper. The percentage of germination, the length of the root and shoot of the seedling as well as the number of root and shoot branches were evaluated. The results were related to the untreated control. The number of seeds in each treatment were between 100 and 200 whereby a statistical evaluation was made possible.

(b) After treatment with the substances under test, the seeds were sown in culture bottles (4 repetitions, 10 to 15 seeds in each repetition) and the height of the shoot, the green weight and the percentage of the germination were evaluated. The results were compared to the untreated control.

(c) The seeds were soaked in solutions containing appropriate concentrations of the dressing composition. After drying the surface, the seeds were sown in culture bottles. The results were compared to the untreated control.

(d) Seeds infected to a known degree were dressed with solutions containing various concentrations of the dressing composition. Twenty dressed seeds each, in 5 repetitions, were put into a Petri-dish on a plate containing Papavisas culture medium. After incubation lasting one week, the number of infected seeds was evaluated.

(e) Treatment of winter wheat seeds in a field experiment:

Before treatment with the dressing composition, the seeds were infected with black-rust (Tilletia sp.) spores which had been collected from the wheat harvest of the preceding year by crushing the ears. The seeds were infected by rotating in a drum mixer for 5 to 10 minutes.

After the infection, the wet dressing was carried out in a Rotadest drum by rotating for 5 to 10 minutes while adding various concentrations of BF-51 and 20 ml of water. After sowing the seeds, the sprouting, plant height, bush formation, green weight and the infectedness by the black-rust of the ears were evaluated.

(f) Treatment of maize seeds in a field experiment:

The wet dressing of the sowing seeds was carried out in a Rotadest drum by rotating for 5 to 10 minutes in the presence of various concentrations of BF-51 and 20 ml/kg of water. After sowing the seeds, the sprouting, plant height, bush formation, green weight and the amount of the crop were evaluated.

EXAMPLE 9

Effect of the composition described in Example 4 on the germination of the winter wheat (Method (a)).

The results are shown in Table I.

TABLE I

| Treatment | Dose | Germination % from 4 × 100 seeds | | | | Average germination % |
|---|---|---|---|---|---|---|
| | | 1 | 2 | 3 | 4 | |
| Untreated | — | 91 | 92 | 95 | 90 | 93 |
| Quinolate-V-4-K | 2 kg/ton | 90 | 91 | 98 | 95 | 91 |
| BF-51 90 WSC | 1 liter/ton | 95 | 93 | 94 | 94 | 94 |
| BF-51 90 WSC | 2 liter/ton | 88 | 91 | 92 | 98 | 90 |
| BF-51 90 WSC | 4 liter/ton | 42 | 46 | 48 | 44 | 45 |
| BF-52 90 WSC | 1 liter/ton | 0 | 0 | 0 | 0 | 0 |

EXAMPLE 10

Effect of the composition described in Example 4 on the germination of the maize (Method (a)).
The results are shown in table II.

TABLE II

| Treatment | Dose | Germination % from 4 × 100 seeds | | | | Average germination % |
|---|---|---|---|---|---|---|
| | | 1 | 2 | 3 | 4 | |
| Untreated | — | 92 | 91 | 90 | 94 | 94 |
| Buvisild K | 2 liters/ton | 95 | 96 | 97 | 96 | 96 |
| BF-51 90 WSC | 1 liter/ton | 95 | 94 | 96 | 95 | 95 |
| BF-51 90 WSC | 2 liters/ton | 95 | 96 | 96 | 97 | 96 |
| BF-51 90 WSC | 4 liters/ton | 50 | 53 | 54 | 51 | 52 |

Tables I and II thus indicate the non-phytotoxic effect of the active ingredient of this invention when utilized at the 1 and 2 liter/ton levels and its availability for use in said treatment.

EXAMPLE 11

The sprouting and development of winter wheat in a field dressing experiment (Method (e)).

TABLE III

| Treatment | Dose | No. of plants pcs/2 m 12/1982 | Bush formation shoot/plant 22/03/1983 | Average height cm | |
|---|---|---|---|---|---|
| | | | | 22/03 | 26/04 |
| Untreated | — | 126.3 | 2.5 | 9.1 | 28.5 |
| Quinolate-V-4-X | 2 kg/ton | 134.3 | 3.0 | 11.7 | 32.5 |
| BF-51 50 WSC | 1 liter/ton | 130.3 | 3.0 | 12.0 | 32.3 |
| BF-51 90 WSC | 2 liters/ton | 136.0 | 3.0 | 11.9 | 32.4 |
| BF-51 90 WSC | 4 liters/ton | 124.0 | 3.0 | 9.9 | 32.2 |

EXAMPLE 12

The sprouting and development of maize in a field dressing experiment (Method (f)).
The results are shown in Table IV.

TABLE IV

| Treatment | Dose | No. of plants from 200 grains 02/05/1983 | Average height cm 25/05 | Eared crop kg/25 m² |
|---|---|---|---|---|
| Untreated | — | 156.0 | 22.02 | 16.0 |
| Buvis.K | 2 kg/ton | 171.3 | 22.01 | 19.3 |
| BF-51 90 WSC | 1 liter/ton | 166.0 | 21.90 | 18.0 |
| BF-51 90 WSC | 2 liters/ton | 169.3 | 22.01 | 20.0 |
| BR-51 90 WSC | 4 liters/ton | 139.3 | 22.04 | 16.3 |

EXAMPLE 13

The combined effect of BF-51 and magnesium sulphate on the germination of wheat grains (Method (b)).
The results are shown in Table V.

TABLE V

| Treatment | Dose | Germination % | Shoot length as % of the control | Green weight as % of the control |
|---|---|---|---|---|
| Untreated | — | 66 | — | — |
| BF-51 90 WSC | 3 liters/ton | 61 | 125 | 146 |
| BF-51 90 WSC | 4 liters/ton | 46 | 122 | 93 |
| BF-51 90 WSC | 5 liters/ton | 44 | 108 | 114 |
| BF-51 90 WSC + 1% by wt. MgSO$_4$ | 3 liters/ton | 66 | 126 | 151 |
| " | 4 liters/ton | 60 | 126 | 139 |
| " | 5 liters/ton | 55 | 120 | 123 |
| MgSO$_4$ | 1% | 80 | 138 | 192 |

EXAMPLE 14

The water uptake of the seeds was measured in such a way that at defined intervals the wheat grains germinating on a wet filter paper were dried by using a hair-drier for 30 seconds in order to remove the humidity from the seed surface and then weighed. The weight increase showed the water uptake of the grains. This experiment is illustrated in FIG. 1.

EXAMPLE 15

Paprika seeds infected with *Rhyzoctonia solani* were treated according to the Method (c), whereupon the plants were sown in culture bottles and cultivated under a foil tent (Method (b)). The activity against Rhyzoctonia was evaluated in the 3 to 4-leaf period of the plants on the basis of the appearance of symptoms as well as the number of stems.
The results are shown in Table VI.

TABLE VI

| Treatment | Germination % | % infection by Rhyzoctonia | Number of plantable individuals as % of the sown seeds |
|---|---|---|---|
| Untreated control | 48 | 18 | 38 |
| BF-51 90 WSC 500 ppm | 66 | 0 | 66 |
| BF-51 90 WSC 1000 ppm | 48 | 0 | 48 |
| BF-51 90 WSC 2000 ppm | 58 | 0 | 58 |

EXAMPLE 16

The effect of BF-51 90 WSC and of Aliette 70 WP (fungicide), respectively against Fusarium species was determined. These investigations were carried out according to the Method (d) on two series of seeds with different susceptabilities to fungus infection.

The results are shown in Table VII.

TABLE VII

| Treatment | Dose kg/ton | Infectedness of the seeds by Furarium |  |
|---|---|---|---|
|  |  | % | % |
| Untreated | — | 12.0 (base infectedness) | 5.0 |
| Aliette 70 WP | 4 | 11.0 | 6.0 |
| BF-51 90 WSC | 1 | 13.0 | 0.0 |
| BF-51 90 WSC | 2 | 8.0 | 0.0 |
| BF-51 90 WSC | 4 | 5.0 | 0.0 |

EXAMPLE 17

The dressing of wheat grains infected by Tilletia species by using BF-51 90 WSC (Method (e)).

The results are shown in Table VIII.

TABLE VIII

| Treatment | Nograd Country | | | | Bekes Country | | | |
|---|---|---|---|---|---|---|---|---|
|  | Dose liter/ton | Total ears/m$^2$ | Infected ears/m$^2$ | Infectedness % | Dose liter/ton | Total ears/m$^2$ | Infected ears/m$^2$ | Infectedness % |
| Untreated infected | — | 2980 | 833 | 27.9 | — | 1924 | 1293 | 67 |
| BF-51 90 WSC | 1 | 3077 | 204 | 6.6 | 1 | 1974 | 1959 | 0.76 |
| BF-51 90 WSC | 2 | 3288 | 91 | 2.7 | 2 | 2002 | 1999 | 0.15 |
| BF-51 90 WSC | 4 | 2992 | 48 | 1.6 | 4 | 1900 | 1898 | 0.009 |

What is claimed is:

1. A seed dressing composition comprising
   (a) 20-90%, by weight, of 3-isononyloxypropyl-ammonium methyl phosphonate as the fungicidal active ingredient;
   (b) 0-5%, by weight, of a surface active agent;
   (c) 0-11.5%, by weight, of an adhesion promoting agent; and
   (d) a sufficient amount of an inert carrier to a total of 100%, by weight, said carrier being present in a minimum concentration of about 5%, by weight.

2. The composition of claim 1, wherein said surface active agent is an alkylaryl polyglycol ether, a fatty acid polyglycol ester or a ligninsulfonate salt.

3. The composition of claim 1, wherein said adhesion promoting agent is partially hydrolyzed polyvinyl acetate, polyvinyl alcohol, carboxymethylcellulose or acacia gum.

4. The composition of claim 1, wherein said carrier is present in a concentration of from 5 to 70%, by weight.

5. The composition of claim 1, wherein said carrier is water, an alcohol, a hydrocarbon solvent or mixture thereof.

6. The composition of claim 5, wherein said carrier is water, methanol, glycerol, xylene or mixtures thereof.

7. A seed dressing fungicidal composition comprising
   (a) 20-90%, by weight, of 3-isononyloxypropyl-ammonium methyl phosphonate as the fungicidal active ingredient;
   (b) 2-10%, by weight, of a magnesium or zinc ion;
   (c) 0-5%, by weight, of a surface active agent;
   (d) 0-16.5%, by weight, of an adhesion promoting agent; and
   (c) a sufficient amount of an inert carrier to a total of 100%, by weight; said carrier being present in a minimum concentration of about 5%, by weight.

8. A method of protecting seeds during their germination period against diseases caused by fungi which comprises applying to the seed prior to or during germination a fungicidally effective amount of the seed dressing composition of claim 1.

9. A method of protecting seeds during their germinative period against diseases caused by fungi which comprises applying to the seed a fungicidally effective amount of the seed dressing composition of claim 7.

10. The method of claim 8, wherein said composition is applied in a concentration of 0.5-3.0 kilograms of active ingredient per ton of seed.

11. The method of claim 9, wherein said composition is applied in a concentration of 0.5-3.0 kilograms of active ingredient per ton of seed.

12. The method of claim 9, wherein said active ingredient and said magnesium or zinc ion are separately applied to said seed.

* * * * *